United States Patent [19]

Ahlers

[11] Patent Number: 5,042,560
[45] Date of Patent: Aug. 27, 1991

[54] METHOD OF PRODUCING OPEN-CELLED METAL STRUCTURES

[75] Inventor: Olaf Ahlers, Hamburg, Fed. Rep. of Germany

[73] Assignee: Eska Medical Lübeck Medizintechnik GmbH & Co., Lübeck, Fed. Rep. of Germany

[21] Appl. No.: 523,083

[22] Filed: May 14, 1990

[30] Foreign Application Priority Data

May 26, 1989 [DE] Fed. Rep. of Germany ....... 3917033

[51] Int. Cl.$^5$ ............... B22C 3/00; B22C 7/02; B22D 23/00; B22D 25/00
[52] U.S. Cl. ........................................ 164/34; 164/45; 264/221
[58] Field of Search ................ 164/34, 35, 36, 45, 164/79; 264/59, 221, DIG. 44

[56] References Cited

U.S. PATENT DOCUMENTS

| 3,845,181 | 10/1974 | Ravault | 264/59 X |
| 3,899,556 | 8/1975 | Heide et al. | 264/DIG. 44 X |
| 3,946,039 | 3/1976 | Walz | 164/34 X |
| 4,600,546 | 7/1986 | Grundei | 164/34 X |
| 4,781,721 | 11/1988 | Grundei | 623/16 |
| 4,812,278 | 3/1989 | Natori et al. | 164/36 X |

FOREIGN PATENT DOCUMENTS

| 3224265 | 1/1984 | Fed. Rep. of Germany. | |
| 1308958 | 3/1973 | United Kingdom | 264/221 |

Primary Examiner—J. Reed Batten, Jr.
Attorney, Agent, or Firm—Panitch Schwarze Jacobs & Nadel

[57] ABSTRACT

A lost positive pattern comprising an open-pored plastics substrate containing pores with an average width of from one to three millimeters is used, in which, after a negative pattern has been made, the voids which it, as a core, contains are filled with metal by casting and the negative pattern is removed. The production of the negative pattern is preceded by the following method steps in which once the substrate of plastics material has been cleaned, it is wetted throughout with a keying resin film which partially dissolves the structure of its surface and in which at least one coat of an auto-crosslinking two-pack silicone is applied onto and into the whole of the substrate of plastics material to thicken the walls and/or the interlinking webs of the porous substrate of plastics material.

11 Claims, 2 Drawing Sheets

METHOD OF PRODUCING OPEN-CELLED METAL STRUCTURES

BACKGROUND OF THE INVENTION a) Field of the Invention

The invention relates to a method of producing open-celled metal structures using a lost positive pattern comprising an open-pored substrate of plastics material containing pores with an average width of from 1 to 3 mm, in which method, after a negative pattern forming a core containing voids has been made, the voids are filled with metal by casting and the negative pattern is finally removed.

b) Description of the Prior Art

A method of this kind, although for producing an implant to serve as a bone replacement, is known from DE-OS 3106917, which corresponds to U.S. Pat. No. 4,781,721. In this case the voids in a sponge of natural or synthetic material forming the positive pattern are filled with a ceramic encapsulating material, the material of the pattern is removed by applying heat and the voids in the negative pattern so obtained are filled with metal. Finally the ceramic core material is removed.

A problem which has arisen with this method is that the walls and the interlinking webs of a natural or synthetic sponge are so weak that the shaped metal body produced by the method is not sufficiently strong.

In DE-OS 32 24 265 (which corresponds to U.S. Pat. No. 4,600,546, the above method is refined by increasing the thickness of the walls and/or the interlinking webs of the pores in the shaped plastics body which is used in this case as the positive model with a deposit of wax, at ambient temperature, either by dipping the pattern in liquified wax or a wax-in-water emulsion or by spraying the pattern with liquified wax or a wax-in-water emulsion, after which water evaporates and the dry wax which is left is then protected with a coating of synthetic lacquer.

Within certain limits, this method allows an open-celled shaped metal body to be produced in which the webs of the cells are thicker than in the shaped body produced by the first method.

However, a disadvantage of this method is that the wax applied onto and into the shaped plastics body by dipping or spraying, combined with the lacquer sprayed onto it, behaves as a rigid structure in comparison with the shaped plastics body, which is elastic, with the result that, under pressure, the wax may separate again slightly from the walls and webs of the pores in the shaped body. Another major disadvantage of this method of application is that the polymeric surfaces of the walls and webs of the shaped plastics body take on a negative charge vis-a-vis the wax or the wax-in-water emulsion. Consequently, there is not a circularly uniform bond between the walls and webs of the shaped plastics body and the wax. This is particularly true of the walls and webs situated within the shaped plastics body in the depthwise direction, or in other words at a distance from its surface. Hence the rheological characteristics of the wax or the wax-in-water emulsion within the shaped body are not sufficiently good to allow the walls and webs within the positive pattern in the depthwise direction to be thickened to a satisfactory degree. As a result the shaped metal body which is produced by this method contains within it walls and webs which are in some cases too thin to withstand the stresses applied in the long term.

Hence against the background which has been outlined, the object of the present invention is to refine the method described above in such a way that the walls and webs of the positive pattern are reliably thickened everywhere, i.e. within the pattern in the depthwise direction as well.

SUMMARY OF THE INVENTION

To this end, the present invention consists in a method of producing open-celled metal structures using a lost positive pattern comprising an open-pored substrate of plastics material containing pores with an average width of from 1 to 3 mm, in which method, after a negative pattern has been made, the voids which it, as a core, contains are filled with metal by casting and the negative pattern is finally removed, in which once the substrate of plastics material has been cleaned, it is wetted throughout with a keying resin film which partially dissolves the structure of its surfaces, and in which at least one coat of an auto-crosslinking two-pack silicone is applied onto and into the whole of the porous substrate of plastics material to thicken the walls and/or interlinking webs of said porous substrate of plastics material.

Hence, once the substrate of plastics material acting as the positive pattern has been cleaned, it is wetted throughout with a keying resin film which partially dissolves the structure of its surfaces, after which at least one coat of an auto-crosslinking two pack silicone is applied onto and into the whole of the porous substrate of plastics material to thicken the walls and/or interlinking webs of said porous substrate of plastics material.

The substrate of plastics material may be cleaned with acetone for example.

The keying resin film can be applied with a spray gun for example. The resin is dissolved in a solvent which evaporates to leave the keying resin film on the structure of the surface of the plastics substrate.

After this the two-pack silicone is applied onto and into the plastics substrate with a spray gun or by dabbing for example.

The use of the keying resin film allows a circular cross-linked bond to come into being between the webs and walls of the plastics substrate and the two-pack silicone.

The cross-linking of the two-pack silicone is followed by the known method steps for producing a negative pattern. This means that, having been treated as described above, the plastics substrate has its pores filled with a ceramic encapsulating medium, which is fired into a core at the same time as the positive pattern is volatilised. The voids in the core are then filled with metal by casting, after which the core material, i.e. the negative pattern, is removed.

It should be emphasised that the open-celled metal structures produced by the method according to the invention can be used for a wide variety of purposes. They may for example form part of a body implant. Compared with an implant to serve as a bone replacement which is produced by the method dissclosed in the above-mentioned DE-OS- 32 24 265, the metal structure produced by the present method has larger pores and, on the outside, sharper edges. Given their size, the larger pores make it possible for bone fibrils to grow deep into them as well. The sharp edges are due to the fact that the probability of cutting through the larger pores when the positive pattern is being cut to size from a plastic substrate is considerably greater than when it is cut to size from a plastics substrate containing smaller pores. On bone implants, the sharp edges on the outer face of an open-celled structure encourage bone to grow into the open-celled structure.

As well as this, it is feasible and advantageous for the structures obtained in accordance with the invention to be used as filters in the form of artifical kidneys.

The method according to the invention may advantageously be refined by adding a further step after the cross-linking of the two-pack silicone. For additional stiffening of the structure of the surfaces of the network of silicone situated in the plastics substrate, a two-pack polyurethane resin may be applied onto and into the plastics substrate. To produce an imtimate bond between the two-pack silicone and the two-pack polyurethane resin which is to be applied the latter has, due to its composition, a property whereby it slightly dissolves the surface of the two-pack silicone.

The keying resin film preferably comprises an unsaturated silicone resin. This produces a system in which an unsaturated silicone resin is paired with the two-pack silicone which is to be applied onto and into the plastic substrate and which will normally be unsaturated also when mixed. This will consistently produce a true pull (attraction) between the silicone resin and the two-pack silicone, as a result of which the webs and walls of the pores in the plastics substrate will be thickened in a particularly impressive manner even within the substrate in the depthwise direction.

The two-pack silicone is advantageously an unsaturated two-pack silicone rubber which cross-links at ambient temperature. Basically the cross-linking may of course also be achieved or accelerated by quenching the plastics substrate carrying the two-pack silicone in water.

It will often be necessary for the walls and/or webs of the pores in the plastics substrate to be thickened by applying a number of coats of the two-pack silicone. When this is done it is advantageous for the individual coats to be of different colours. In this way it becomes possible for the thickness of the coats to be seen, under a magnifying glass for example, so that they can be checked for consistent thickness.

This check serves to ensure the quality of the open-celled metal structures produced by the method according to the invention. Once the method has been carried out, an even thickening of the walls and/or the cross-linked webs of the pores is reflected in the uniformity of the walls and/or webs of the metal structure.

The invention also consists in an open-celled metal structure made by any of the methods defined hereinabove.

BRIEF DESCRIPTION OF THE DRAWINGS

The advantages of the method according to the invention over the prior art method are evident from the product produced by the method of the invention. Because of this the said advantages will be explained by reference to the accompanying drawings which are diagrammatic representations of open-celled metal structures, of which:

FIG. 1b is a plan view of the prior art covering shown in FIG. 1a,

FIG. 2b is a plan view of the covering shown in FIG. 2a.

Figure 1A:
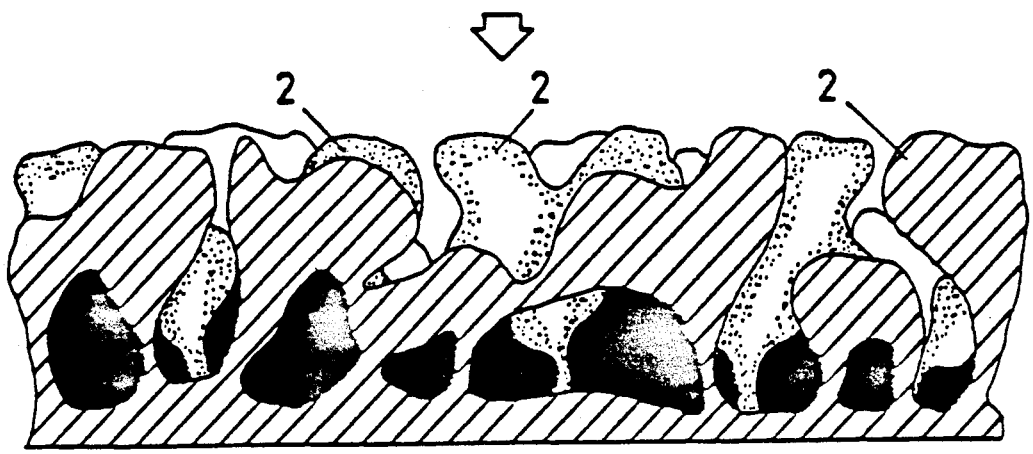
FIG. 1a is a diagrammatic representation of a section through a prior art open-celled covering or structure produced by the known method which has been used in the past.
Figure 1B:
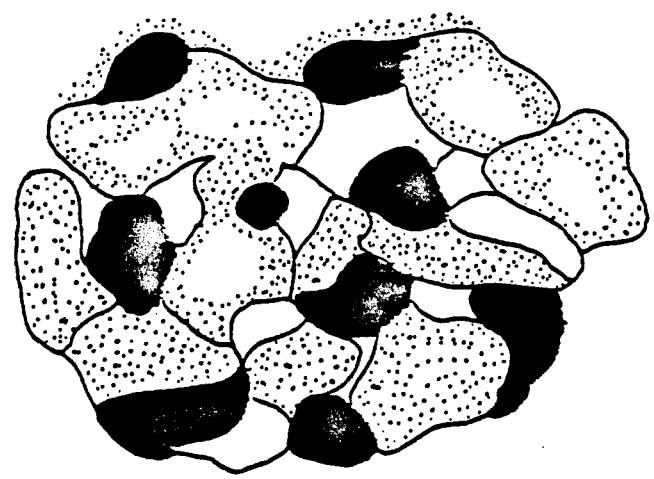
Figure 2A:
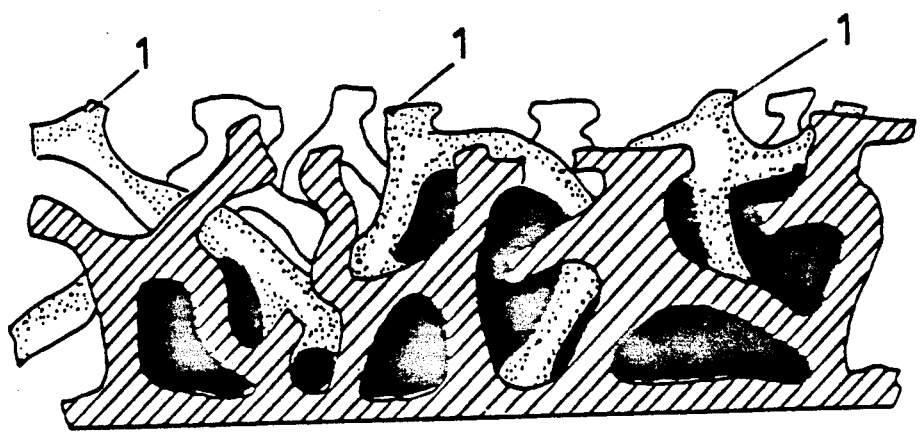
FIG. 2a is a diagrammatic representation of a section through an open celled covering or structure produced by the method of the invention.

The black portions depicted in FIGS. 1a and 1b and 2a and 2b represent cavities or pores present in the structure. The white portions in FIGS. 1a and 1b and 2a and 2b represent the walls and interlinking webs of the metal structures. The dotted white portions represent walls and interlinking webs of the metal structures which are closer to the viewer relative to the walls and webs represented by the solid white portions. Likewise, the hatched white portions in FIGS. 1a and 2a are closet to the viewer relative to the dotted and plain white portions, respectively.

DESCRIPTION OF THE PREFERRED EMBODIMENT

As can clearly be seen from the prior art covering in FIG. 1a, the walls and interlinking webs of the pores become smaller as depth increases (in the, direction of the arrow shown). As mentioned above, this is due to the poorer rheological characteristics of the liquid wax or the wax-in-water emulsion within the shaped plastics body which is used as the positive pattern.

In FIG. 2a, on the other hand it can clearly be seen that in the structure produced according to the method of the present invention the walls and webs are of adequate thickness even at depth. As explained above, this is a result of applying a keying resin film onto and into the plastics substrate used as the positive pattern, combined with the thickening of the walls and interlinking webs of the plastics substrate by a two-pack silicone.

FIG. 1b is a plan view of a structure produced by the known method. It is clear that a very large amount of material has remained in the surface and is absent elsewhere, namely at depth. What is more, the pores in the structure are relatively small. Under certain circumstances, this will make it more difficult for bone fibrils to grow into the structure when it is part of a bone implant.

Figure 2B:
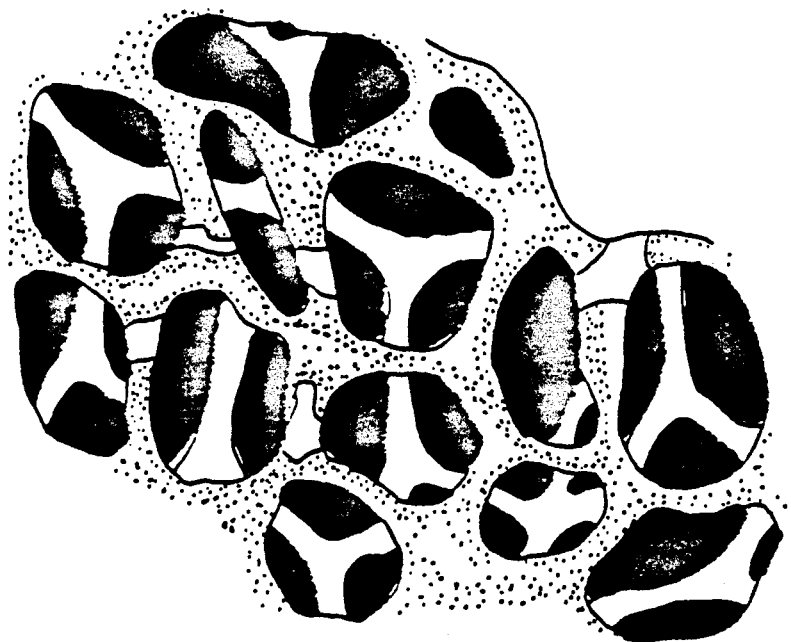

By contrast, it can clearly be seen from FIG. 2b that the major proportion of the material is not concentrated at the surface of the structure. What is more, the pores or cells of the structure are relatively large. If the structure is used for bone implants for example, it is perfectly possible for bone fibrils to grow in. Finally, attention should be drawn to a certain sharpness shown by the edges at the surface of the structure produced by the method of the present invention, this being due to the presence of jagged projections 1. The surface of the structure produced by the known method on the other hand is relatively "blunt" because all that project outwards are rounded protusions 2.

What is claimed is:

1. A method of producing open-called metal structures using a lost positive pattern comprising an open-pored substrate of plastics material having a structure of surfaces and containing pores with an average width of from 1 to 3 mm, in which method, after a negative pattern forming a core containing voids has been made, the voids are filled with metal by casting and the negative pattern is finally removed, said method comprising the steps of:

a) cleaning the substrate of plastics material, b) wetting the substrate of plastics material throughout with a keying resin film which partially dissolves the structure of the surfaces of the substrate of plastics material, and c) applying at least one coat of auto-crosslinking two-pack silicone onto and into the whole of the open-pored substrate of plastics material whereby to thicken at least one of the walls and interlinking webs of said open-pored substrate of plastics material, wherein said steps (a) to (c) are performed before the negative pattern has been made.

2. The method according to claim 1, and comprising the additional step of:

d) stiffening further the structure of surfaces of the substrate of plastics material by a two-pack polyurethane resin after cross-linking of the two-pack silicone.

3. The method according to claim 1, wherein the keying resin film comprises an unsaturated silicone resin.

4. The method according to claim 2, wherein the keying resin film comprises an unsaturated silicone resin.

5. The method according to claim 1, wherein the two-pack silicone is an unsaturated two-pack silicone rubber which cross-links at ambient temperature.

6. The method according to claim 2, wherein the two pack silicone is an unsaturated two-pack silicone rubber which cross-links at ambient temperature.

7. The method according to claim 3, wherein the two-pack silicone is an unsaturated two-pack silicone rubber which cross-links at ambient temperature.

8. The method according to claim 1, wherein more than one coat of the two-pack silicone is applied onto and into the substrate of plastics material to provide a plurality of individual coats which each have a thickness and which are of different colours to allow the thickness of each coat to be seen.

9. The method according to claim 2, wherein more than one coat of the two-pack silicone is applied onto and into the substrate of plastics material to provide a plurality of individual coats which each have a thickness and which are of different colours to allow the thickness of each coat to be seen.

10. The method according to claim 3, wherein more than one coat of the two-pack silicone is applied onto and into the substrate of plastics material to provide a plurality of individual coats which each have a thickness and which are of different colours to allow the thickness of each coat to be seen.

11. The method according to claim 5, wherein more than one coat of the two-pack silicone is applied onto and into the substrate of plastics material to provide a plurality of individual coats which each have a thickness and which are of different colours to allow the thickness of each coat to be seen.

* * * * *